US010806779B2

(12) United States Patent
Dong et al.

(10) Patent No.: US 10,806,779 B2
(45) Date of Patent: Oct. 20, 2020

(54) METHOD FOR PREPARING VIROSOMES

(71) Applicant: Janssen Vaccines & Prevention B.V., Leiden (NL)

(72) Inventors: Wenyu Dong, Leiden (NL); Pieter Rijken, Leiden (NL); Mike Ugwoke, Leiden (NL)

(73) Assignee: JANSSEN VACCINES & PREVENTION B.V., Leiden (NL)

( * ) Notice: Subject to any disclaimer, the term of this patent is extended or adjusted under 35 U.S.C. 154(b) by 384 days.

(21) Appl. No.: 14/392,330

(22) PCT Filed: Jun. 30, 2014

(86) PCT No.: PCT/EP2014/063813
§ 371 (c)(1),
(2) Date: Dec. 23, 2015

(87) PCT Pub. No.: WO2015/000831
PCT Pub. Date: Jan. 8, 2015

(65) Prior Publication Data
US 2016/0199480 A1 Jul. 14, 2016

(30) Foreign Application Priority Data

Jul. 2, 2013 (EP) .................................... 13174691

(51) Int. Cl.
*C12N 7/02* (2006.01)
*A61K 39/12* (2006.01)
(Continued)

(52) U.S. Cl.
CPC ............ *A61K 39/12* (2013.01); *A61K 9/1271* (2013.01); *A61K 39/145* (2013.01); *C12N 7/00* (2013.01);
(Continued)

(58) Field of Classification Search
None
See application file for complete search history.

(56) References Cited

U.S. PATENT DOCUMENTS 5,057,540 A    10/1991    Kensil et al.
7,901,920 B2    3/2011    Huckriede et al.
(Continued)

FOREIGN PATENT DOCUMENTS

EP    1676569 A1    7/2006
WO    9003184 A1    4/1990
(Continued)

OTHER PUBLICATIONS

Mastrobattista et al., "Preparation of influenza virosomes by post-insertion of influenza virus spike proteins into preformed liposomes"[Online], pp. 122-140, XP002349823, Retrieved from the Internet: URL: https://dspace.library.uu.nl/bitstream/handle/1874/329/c4.pdf, (Year: 2001).*

(Continued)

*Primary Examiner* — M Franco G Salvoza
(74) *Attorney, Agent, or Firm* — Kramer Amado, P.C.

(57) ABSTRACT

Described are methods for preparing virosomes comprising the steps of: (a) providing an enveloped virus, and optionally inactivating the virus; (b) solubilizing the viral envelopes in a first solubilizing agent; (c) pre-solubilizing exogenous components in a second solubilizing agent; (d) adding the pre-solubilized exogenous components to the solubilized viral envelopes; and (e) reconstituting virosomal membranes by removing the solubilizing agent. According to the disclosure, the viral envelopes and the exogenous components are (pre-)solubilized at a temperature below 33° C.

16 Claims, 3 Drawing Sheets

(51) Int. Cl.
  C12N 7/00      (2006.01)
  A61K 39/145    (2006.01)
  A61K 9/127     (2006.01)
  A61K 39/00     (2006.01)
(52) U.S. Cl.
  CPC ........... A61K 2039/5258 (2013.01); A61K 2039/55555 (2013.01); A61K 2039/70 (2013.01); C12N 2760/16134 (2013.01); C12N 2760/16151 (2013.01); C12N 2760/16234 (2013.01); C12N 2760/16251 (2013.01)

(56) References Cited

U.S. PATENT DOCUMENTS

| | | |
|---|---|---|
| 2006/0193873 A1 | 8/2006 | Stegmann et al. |
| 2006/0228376 A1 | 12/2006 | Huckriede et al. |
| 2008/0268028 A1 | 10/2008 | Zurbriggen et al. |
| 2009/0087453 A1 | 4/2009 | Moser et al. |
| 2009/0202622 A1 * | 8/2009 | Fleury ............. A61K 9/0019 424/450 |
| 2009/0263470 A1 | 10/2009 | Coller et al. |
| 2009/0022762 A1 | 11/2009 | Galarza et al. |
| 2011/0045057 A1 * | 2/2011 | Zurbriggen ......... A61K 9/127 424/450 |
| 2014/0072616 A1 | 3/2014 | Zurbriggen et al. |

FOREIGN PATENT DOCUMENTS

| | | | |
|---|---|---|---|
| WO | WO-9219267 A1 * | 11/1992 | ........... A61K 9/1271 |
| WO | 9611711 A1 | 4/1996 | |
| WO | 2004004762 A1 | 1/2004 | |
| WO | 2004071492 | 8/2004 | |
| WO | 2004110486 A1 | 12/2004 | |
| WO | 2005002620 A1 | 1/2005 | |
| WO | 2006069719 | 7/2006 | |
| WO | 2007130330 | 11/2007 | |
| WO | WO-2009000433 A1 * | 12/2008 | ........... A61K 9/127 |
| WO | 201500832 A1 | 3/2014 | |
| WO | 201500831 A1 | 6/2014 | |

OTHER PUBLICATIONS

Bron et al., "Preparation, Properties, and Applications of Reconstituted Influenza Virus Envelopes (Virosomes)", Methods in Enzymology, vol. 220: 313-331 (Year: 1993).*
Gluck et al., Immunopotentiating Reconstituted Influenza Virus Virosome Vaccine Delivery System for Immunization against Hepatitis A, J. Clin. Invest., Dec. 1992, pp. 2491-2495, vol. 90.
Huckriede et al., The virosome concept for influenza vaccines, Vaccine, 2005, pp. S1/26-S1/38.
Cornet et al., Virosomes Reconstituted from Human Immunodeficiency Virus Proteins and Lipids, Biochemical and Biophysical Research Communications, Feb. 28, 1990, pp. 222-231, vol. 167, No. 1, Academic Press Inc., Orlando, FL, US.
Munoz-Barroso et al., Dynamic Properties of Newcastle Disease Virus Envelope and Their Relations with Viral Hemagglutinin-neuraminidase Membrane Glycoprotein, Biochimica et Biophysica Acta, 1997, pp. 17-31, vol. 1327, Elsevier, Amsterdam, NL.
Zurbriggen et al., IRIV-adjuvanted Hepatitis A Vaccine: in vivo Absorption and Biophysical Characterization, Progress in Lipid Research, 2000, pp. 3-18, vol. 39, Pergamon Press, Paris, FR.
PCT International Search Report, PCT/EP2014/063813, dated Sep. 2, 2014.
Mengiardi et al., Virosomes as carriers for combined vaccines, Vaccine, Oct. 1, 1995, p. 1306-15, vol. 13, No. 14, Elsevier Ltd, GB.
Mischler et al., Inflexal V a trivalent virosome subunit influenza vaccine: production, Vaccine, Dec. 20, 2002, pp. B17-B23, vol. 20, Elsevier Ltd, GB.
Glueck et al., Immunogenicity of New Virosome Influenza Vaccine in Elderly People, Lancet, Jul. 16, 1994, pp. 160-163, vol. 344, No. 8916, Little, Brown & Co., Boston, US.
Wilschut et al., Influenza vaccines: The virosome concept, Immunology Letters, Feb. 21, 2009, pp. 118-121, vol. No. 2, Elsevier BV, NL.
PCT International Written Opinion, PCT/EP2014/063813, dated Sep. 2, 2014.
Gluck, et al., "Safety and Immunogenicity of Intranasally Administered Inactivated Trivalent Virosome-Formulated Influenza Vaccine Containing *E. Coli* Heat-Labile Toxin as a Mucosal Adjuvant", Journal of Infectious Diseases 2000 (181) March, pp. 1129-32.

* cited by examiner

METHOD FOR PREPARING VIROSOMES

CROSS-REFERENCE TO RELATED APPLICATIONS

This application is a national phase entry under 35 U.S.C. § 371 of International Patent Application PCT/EP2014/063813, filed Jun. 30, 2014, designating the United States of America and published in English as International Patent Publication WO 2015/000831 A1 on Jan. 8, 2015, which claims the benefit under Article 8 of the Patent Cooperation Treaty to European Patent Application Serial. No. 13174691.9, filed Jul. 2, 2013.

TECHNICAL FIELD

The disclosure relates to the field of medicine. The disclosure, in particular, relates to methods for preparing virosomes and to virosome preparations obtainable by such methods.

BACKGROUND

Virosomes are reconstituted phospholipid (PL) membranes containing proteins from a virus, like hemagglutinin (HA) and neuraminidase (NA) from an influenza virus. These virosomes may be derived from influenza viruses, or from other enveloped viruses, such as, but not limited to, the following families: flaviviridae (e.g., Dengue virus, Hepatitis C virus HEV, Japanese encephalitis virus, Yellow fever virus, West Nile virus), Poxviridae (i.e., Cowpox virus, Monkeypox virus, vaccinia virus, Variola virus), Retroviridae (i.e., immunodeficiency viruses HIV/SIV), paramyxoviridae (i.e., Measles virus, Mumps virus, Parainfluenza viruses, metapneumovirus, Respiratory Syncytial virus RSV), and Orthomyxoviridae (i.e., influenza viruses). Since virosomes do not contain the viral genomic material (e.g., viral RNA or DNA), they are non-replicative in nature, which renders them safe for administration to animals and humans in the form of an immunogenic composition (e.g., as a vaccine), or as an adjuvant, or as drug (protein) delivery vesicle with or without targeting ligands. Virosomes thus have been especially useful in the field of vaccination, where it is desired to stimulate an immune response to an antigen or antigens associated with a particular disease or disorder. In such cases, an antigen (or antigens) is typically encapsulated or embedded in the virosome or associated with virosome, which then delivers this antigen or the antigens to the host immune system of the subject to be vaccinated.

Virosomes are generally produced from a solubilized virus fraction using either of two different approaches, one approach involving the addition of exogenous lipids to the solubilized virus fraction (as described in, e.g., US 2009/0263470, US 2009/0087453) prior to reconstitution of the virosomal membranes, and the other approach being based on reconstituting the viral membrane without the addition of exogenous lipids (e.g., as described in U.S. Pat. No. 7,901,920).

When exogenous lipids are used for virosome production, solubilization of these lipids and blending the lipids with the viral protein solution is a critical technical step. The current method for the preparation of virosomes using exogenous lipid components involves solubilizing of the exogenous lipids (e.g., (egg-derived) phosphatidylcholine (PC)) together with the viral antigens in a detergent solution, either before or after ultracentrifugation, followed by ultrasonication at elevated temperatures of between 33° C. and 37° C. or even higher (e.g., as described in US 2009/0263470, and US 2009/0087453). Complete solubilization is often a lengthy process (>80 minutes), typically requiring ultrasonication and manual mixing (with syringes) at elevated temperature. The steps of ultrasonication and syringe mixing at elevated temperatures put a lot of stress (both shear and thermal stress) on the antigen proteins (e.g., HA and NA) as well as on the phospholipids.

Due to the increasing world population, growing and emerging economies, and intensified international traveling, the demand for vaccines, including virosomal vaccines, is still growing. There is, thus, an ongoing need for improved and efficient methods for preparing virosomes.

BRIEF SUMMARY

Provided are improved methods for preparing virosomes. The methods, in particular, comprise the steps of (a) providing an enveloped virus and optionally inactivating the virus; (b) solubilizing the viral envelopes in a first solubilizing agent; (c) pre-solubilizing exogenous components in a second solubilizing agent, (d) adding the pre-solubilized exogenous components to the solubilized viral envelopes; and (e) reconstituting virosomal membranes by removing the solubilizing agent or agents, wherein the viral envelopes and the exogenous components are (pre-)solubilized at a temperature below 33° C.

According to the disclosure, the first and second solubilizing agents may be the same or different solubilizing agents.

In certain embodiments, the exogenous components are exogenous lipids, such as phospholipids. In certain embodiments, the exogenous components are components, which improve and/or alter the physicochemical properties, stability, drug delivery, and/or immunogenic properties of the virosome preparation.

The disclosure further relates to virosomes obtainable by the method according to the disclosure, to compositions comprising the virosomes, and uses thereof, e.g., for eliciting an immune response in a subject, e.g., an immune response against influenza viruses or other viruses, for potentiating an immune response (e.g., as adjuvants), or as a drug targeting vesicle, or as therapeutic agents (with drug encapsulated or inserted in membrane). In a preferred embodiment, the composition is a vaccine. The compositions me preferably suitable for human administration. The compositions may be used in methods of preventing and/or treating any viral disease, in particular, but not limited to, those caused by influenza virus. The disclosure further relates to the use of the virosomes as a vaccine and/or as an adjuvant. The disclosure, in particular, relates to the use of the virosomes as a vaccine for the prevention and/or treatment of influenza.

DETAILED DESCRIPTION

This disclosure relates to improved methods for preparing virosomes.

This disclosure, in particular, provides a method for preparing virosomes, the method comprising the steps of: (a) providing an enveloped virus, and optionally inactivating the virus; (b) solubilizing the viral envelopes in a first solubilizing agent; (c) pre-solubilizing exogenous components in a second solubilizing agent; (d) adding the pre-solubilized exogenous components to the solubilized viral envelopes; and (e) reconstituting virosomal membranes by removing the solubilizing agent(s), wherein the viral envelopes and the exogenous components are (pre-) solubilized in the solubilizing agent(s) at a temperature below 33° C. The method according to this disclosure is short, mild, robust, scalable, and more reproducible and controllable as compared to the current methods used in the prior art.

As described herein, the term "virosome" refers to a reconstituted lipid-containing membrane, containing viral envelope proteins (antigens), such as, but not limited to, hemagglutinin and/or neuraminidase in the case of an influenza virus, incorporated in the virosomal membrane, but without having the genetic background of the virus itself (see, e.g., Glück 1992; Huckriede et al. 2005).

An "enveloped virus" is a virus in which the virus core is surrounded by a lipid-rich outer coat containing viral proteins. Amongst such viruses are viruses from, but not limited to, the following families: flaviviridae (e.g., dengue virus, Hepatitis C virus, hepatitis E virus, Japanese encephalitis virus, Yellow fever virus, West Nile virus), Poxviridae (e.g., Cowpox virus, Monkeypox virus, vaccinia virus, Variola virus), Retroviridae (e.g., immunodeficiency viruses HIV/SIV), paramyxoviridae (e.g., Measles virus, Mumps virus, Parainfluenza viruses, metapneumovirus, Respiratory Syncytial virus RSV), and Orthomyxoviridae (e.g., Influenza viruses) for example.

The term "virosomal membrane" as used herein refers to a membrane structure that is reconstituted in vitro and that is composed of a lipid bilayer (derived from the viral envelope, with or without additional exogenous lipids) with integrated viral envelope proteins. The term "envelope protein" refers to protein that is encoded by an enveloped virus and that is normally present on the viral membrane.

By "exogenous components" is meant any additional component(s) not endogenous to the virus but added to the virus components during preparation of the virosomes. Preferably, the exogenous components are exogenous lipids. Preferably, the exogenous component remains associated with the virosomes after preparation thereof.

By "exogenous lipid" is meant a lipid that is not endogenous to the virus but is added to the virus components during preparation of the virosomes.

Figure 1:
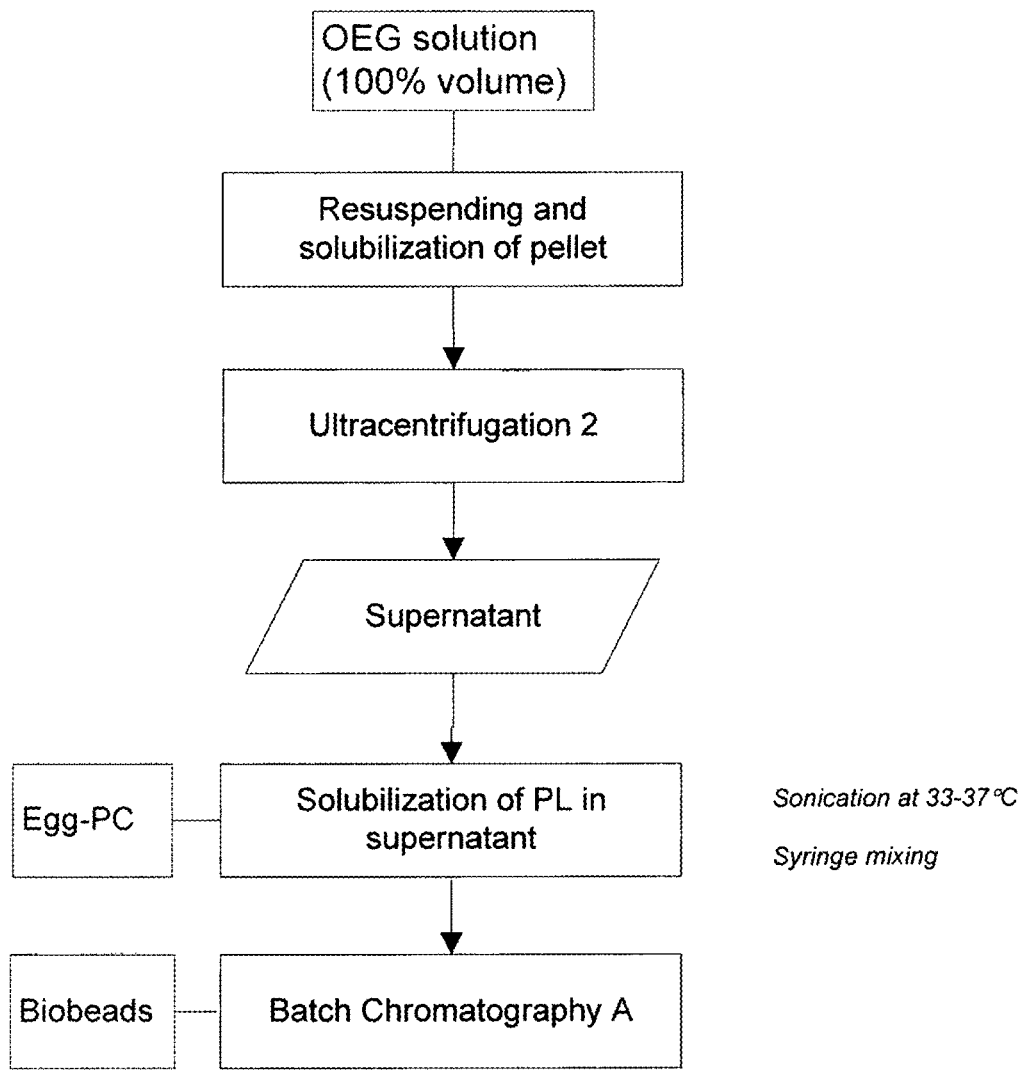
FIG. 1 shows a flow chart showing the steps of solubilizing the exogenous lipids (PL) according to the prior art.

Virosomes are known in the art and are typically produced by diluting monovalent whole-virus pools (optionally inactivated) with, e.g., phosphate-buffered saline (PBS) followed by ultracentrifugation. The pellets of the ultracentrifuged whole virus preparations are then solubilized with a solubilizing agent, e.g., octaethylene glycol monododecyl ether (OEG) or TRITON® X-100 or a mixture of solubilizing agents. The solubilized preparations are subsequently subjected to another ultracentrifugation step. When exogenous lipids are to be added, the supernatants are mixed with exogenous lipids (e.g., egg-derived lecithin) for solubilization. Generally, in order to achieve complete solubilization, which is required to obtain uniform distribution of the lipid with viral membrane components, ultrasonication and/or manual mixing (e.g., with syringes) at an elevated temperature of about 33° C. to 37° C. are needed. After solubilization, the solubilizing agent is removed, e.g., by batch-chromatography, in order to reconstitute virosomal membranes comprising virus-derived antigen, viral membrane lipids and exogenous lipids (see FIG. 1). Inactivation of the virus is generally achieved by use of formaldehyde or beta propiolactone (BPL).

As described above, the current duration of the solubilization step, however, is relatively long (>80 minutes) and ultrasonication and manual mixing (e.g., with syringes) at elevated temperatures are needed. The steps of ultrasonication and syringe mixing at elevated temperatures put a lot of stress (both shear and thermal stress) on the protein antigens (e.g., HA and NA) as well as on the phospholipids. The process, therefore, is not readily scalable and controllable, with complete solubilization being harder to achieve in larger batch sizes. Complete solubilization is difficult to determine and/or control, which can have impact on the quality of the final product (e.g., virosome particle size, antigen spike density, and spiking efficiency). Moreover, these steps generate a lot of foam and it is well known that protein exposure to large air-liquid interfaces in foam formed has destabilizing effects on protein. In addition, ultrasonication can induce radical formation, which, for instance, can lead to antigen oxidation and/or to phospholipid (PL) oxidation, especially when the phospholipids contain unsaturated fatty acids.

It has now been surprisingly shown that complete solubilization of exogenous components, such as exogenous lipids, can be achieved and controlled under very gentle process conditions. Thus, it has been shown that solubilization can be performed at a temperature below 33° C. In addition, sonication to achieve complete solubilization is not necessary, which will help to preserve the stability of antigen proteins (e.g., HA and NA) and the phospholipids.

Figure 2:
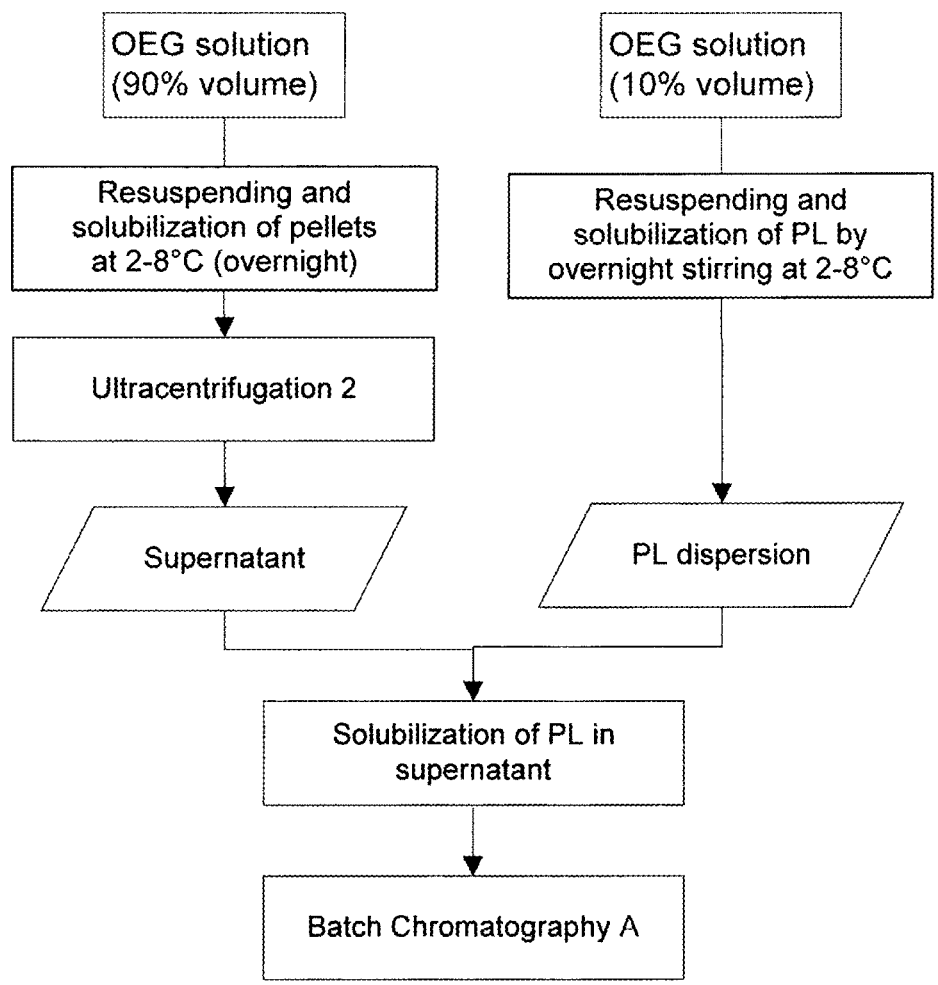
FIG. 2 shows the process steps according to an embodiment of this disclosure.
Figure 3:
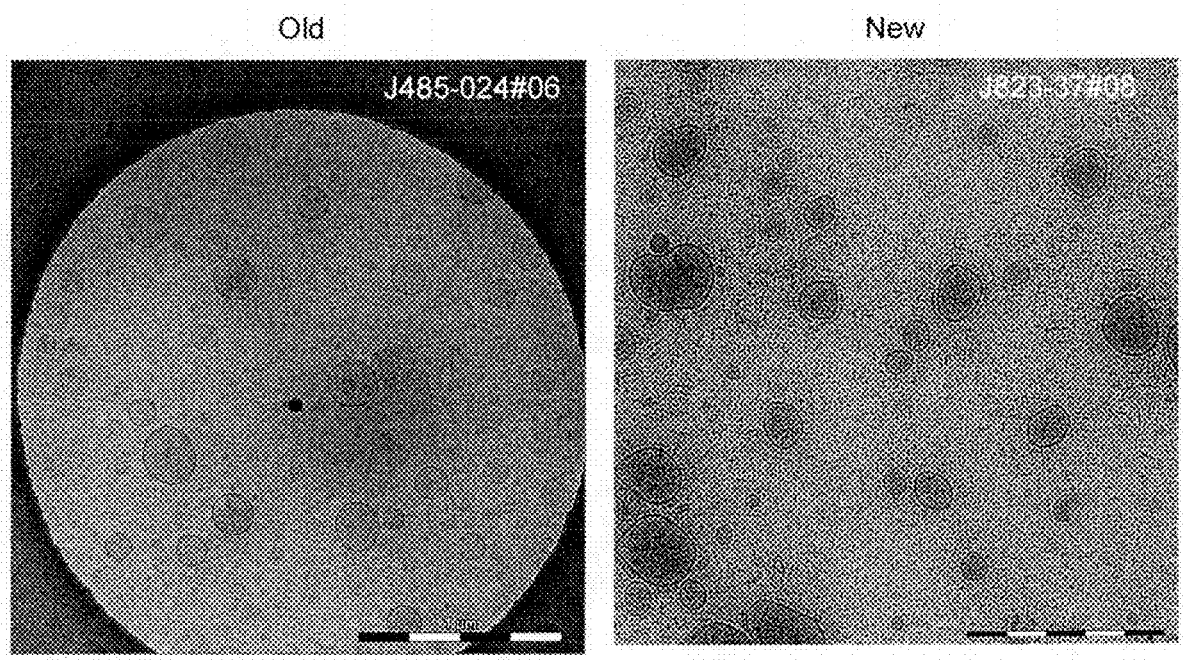
FIG. 3 shows TEM micrographs of virosomes manufactured using the method known in the art (old) and the method according to this disclosure (new), with the latter showing an increased spiking of the virosomes by HA.

Thus, the exogenous components, such as exogenous lipids, are pre-suspended and/or pre-solubilized at a temperature below 33° C., preferably below 32° C., 31° C., 30° C., 27° C., 25° C., 20° C., 18° C., 15° C. or below 10° C. In certain embodiments, the exogenous components, such as lipids, are pre-suspended and/or pre-solubilized at room temperature. In a preferred embodiment, the exogenous components, such as lipids, are pre-suspended and/or pre-solubilized at a temperature of between 0 and 10° C., preferably between 2° C. and 8° C. Subsequently, the exogenous components (such as phospholipids) are quickly and completely solubilized after gentle blending (e.g., magnetic stirring) with the supernatant containing the viral envelope protein (e.g., hemagglutinin (HA) and/or neuraminidase (NA) when influenza virus is used; see FIG. 2), again preferably at a temperature below 33° C., preferably below 33° C., 32° C., 31° C. 30° C., 27° C., 25° C., 20° C., 18° C., 15° C. or below 10° C. Virosomes obtained using the method according to the disclosure have been shown to have an immunogenicity that is at least equivalent to the immunogenicity of virosomes obtained using the method of the prior art. In addition, the amount of virosomes with spiked antigen may be increased.

In certain embodiments, the first and second solubilizing agents are the same.

In certain embodiments, the viral envelopes are solubilized using from 25% to 99% of the total amount of the solubilizing agent and the exogenous components (such as phospholipids) are pre-solubilized using from 1% to 75% of the total amount of the solubilizing agent. In other embodiments, the viral envelopes are solubilized using from 75% to 95% of a total amount of the solubilizing agent and the exogenous components (such as phospholipids) are pre-solubilized using from 5% to 25% of the total amount of the solubilizing agent. In a particular embodiment, the viral envelopes are solubilized using about 90% of a total amount of solubilizing agent and the exogenous phospholipids are pre-solubilized using about 10% of the total amount of the solubilizing agent. According to the disclosure, it has been shown that antigen recovery of the inactivated virus bulk is not impacted by using 25% or more, in particular, 90% of the total volume of the solution of solubilizing agent.

According to the disclosure, the new method is applicable to a broad range of concentrations of the solubilizing agent and combination of solubilizing agents. In certain embodiments, the solubilizing agent is used in a concentration of about 10 mM to 1000 mM. In particular embodiments, the solubilizing agent is used in a concentration of about 25 mM to 250 mM, preferably in a concentration of 50 mM to 150 mM, and even more preferably in a concentration of 100 mM.

In a particular embodiment, the solubilizing agent is a non-ionic surfactant, such as octaethylene glycol monododecyl ether (OEG). However, the solubilizing agent may also be selected from surfactants like TRITON®, Tergitol-type NP-40, Octyl glucoside, Pentaethylene glycol monododecyl ether; organic solvents such as, but not limited to, methanol, ethanol, chloroform, dimethyl sulfoxide, n-methyl pyrolidinone, tetrahydrofuran, etc.

In certain embodiments, the exogenous components are exogenous lipids. The exogenous lipids may comprise neutral and charged (phospho)lipids, steroid-derived lipids, neutral and charged synthetic lipids.

In certain embodiments, the exogenous components are phospholipids, such as egg-derived phospholipids only, in order to minimize the complexity of the formulation. In certain embodiments, the exogenous phospholipids are selected from the group consisting of (synthetic or natural) phosphatidylcholine (PC), phosphatidylethanolamine, phosphatidylserine, phosphatidylglycerol pegylated lipids, and cardiolipin. In a preferred embodiment, the exogenous lipids are egg phosphatidylcholine (PC), 1,2-dipalmitoyl-sn-glycero-3-phosphocholine (DPPC), Monophosphoryl Lipid A (MPLA, GLA), Dimethyldioctadecylammonium (Bromide Salt) (DDAB), 1,2-Dioleoyl-3-Trimethylammonium-Propane (DOTAP), or 1,2-Dioleoyl-3-dimethylammonium-propane (DODAP).

According to the disclosure, a broad range of exogenous components can be integrated or inserted in the virosomal membrane. Other exogenous components that can be used according to the disclosure include, but are not limited to, neutral and charged lipoproteins, neutral and charged lipopolysaccharides, adjuvants and/or targeting ligands.

In certain embodiments, the method may comprise a further step of adding one or more viral antigens.

Using the method of this disclosure, virosomes having a uniform distribution of envelope protein/antigen (e.g., HA) are obtained. In addition, it has been suggested that virosomes may be obtained having a higher so-called spike density (i.e., number of envelope protein/antigen molecules per virosome surface unit area) as compared to the spike density of virosomes obtained using methods of the prior art. In addition, the method according to the disclosure may result in a higher so-called spike efficiency (proportion of envelope protein/antigen taken into the virosome of the total amount of envelope protein/antigen in the starting suspension expressed as number of spikes per particle), as compared to the methods of the prior art. Further, the method may result in less empty phospholipid particles. This may further increase the immunogenicity and stability of the antigen since more of it will be in the virosomal membrane and less as aggregates in suspension.

In certain embodiments, the method further comprises the step of purifying the reconstituted virosomes. Purification of the virosomes may be accomplished using standard techniques known in the art, such as, but not limited to, batch chromatography (with, for example, BIOBEADS®), affinity chromatography, gel filtration, dialysis, cross-flow filtration, etc.

In certain embodiments, the method further comprises the step of size reduction of the reconstituted virosomes by techniques such as, but not limited to, (high pressure) homogenization, static mixing, micromixing, microfluidizing, and extrusion.

This disclosure also relates to virosomes obtainable by a method as described herein.

The disclosure furthermore relates to compositions comprising the above-described virosomes. The disclosure further provides (immunogenic) compositions comprising a therapeutically effective amount of virosomes described herein. The (immunogenic) compositions may further comprise a pharmaceutically acceptable excipient. By "pharmaceutically acceptable excipient" is meant any inert substance that is combined with an active molecule for preparing an agreeable or convenient dosage form. The "pharmaceutically acceptable excipient" preferably is an excipient that is non-toxic to recipients at the used dosages and concentrations, and is compatible with other ingredients of the formulation. Pharmaceutically acceptable excipients are widely applied and known in the art (see *Remington's Pharmaceutical Sciences,* 18th edition, A. R. Gennaro, Ed., Mack Publishing Company [1990]; *Pharmaceutical Formulation Development of Peptides and Proteins,* S. Frokjaer and L. Hovgaard, Eds., Taylor & Francis [2000]; and *Handbook of Pharmaceutical Excipients,* 3rd edition, A. Kibbe, Ed., Pharmaceutical Press [2000]). The exact formulation should suit the mode of administration.

In certain embodiments, the immunogenic compositions may comprise, or are administered in combination with, an adjuvant. The adjuvant may be administered before, concomitantly with, or after administration of the composition. In another embodiment, the adjuvant can be inserted into the virosome membrane. Examples of suitable adjuvants include, but are not limited to, saponin formulations, such as, for example, QS21 and immunostimulating complexes (ISCOMS) (see, e.g., U.S. Pat. No. 5,057,540; WO 90/03184, WO 96/11711, WO 2004/004762, WO 2005/002620); bacterial or microbial derivatives, examples of which are monophosphoryl lipid A (MPL), 3-O-deacylated MPL (3dMPL), CpG-motif containing oligonucleotides, ADP-ribosylating bacterial toxins or mutants thereof, such as *E. coli* heat labile enterotoxin LT, cholera toxin CT, pertussis toxin PT, or tetanus toxoid TT, Trehalose dibehenate (TDB) and Matrix M (Isconova). However, since virosomes may have intrinsic adjuvanting activity, in certain embodiments, the immunogenic compositions of this disclosure do not comprise additional adjuvants. Such additional adjuvants might give rise to side effects, which are thus circumvented according to this embodiment of the disclosure. Such side effects may also be reduced when the adjuvant is inserted into the membrane.

The disclosure also relates to methods for inducing and/or increasing an immune response in a subject, the method comprising administering to a subject the above-described virosomes and/or immunogenic compositions. According to the disclosure, the induced immune response may be directed against the viral envelope protein and/or to the additional (viral) antigen(s). A subject according to the disclosure preferably is a mammal, e.g., mouse, pig, ferret, non-human primate, or a human, that is capable of being infected with an infectious disease-causing virus, for instance, an influenza virus. Preferably, the subject is a human subject.

The term "therapeutically effective amount" as described herein refers to an amount of virosomes that is effective for preventing, ameliorating and/or treating a condition resulting from infection with a virus, in particular, an influenza virus. "Amelioration" as used herein may refer to the reduction of visible or perceptible disease symptoms, viremia, or any other measurable manifestation of the viral infection, in particular, the influenza infection. Prevention encompasses inhibiting or reducing the spread of virus or inhibiting or reducing the onset, development or progression of one or more of the symptoms associated with infection with the virus, in particular, influenza virus.

The invention also relates to the above-described virosomes and/or (immunogenic) compositions for inducing and/or increasing an immune response in a subject, in particular, for use as a vaccine and/or as an adjuvant. The virosomes thus may be used to elicit neutralizing antibodies against the viral envelope protein, e.g., to HA and/or NA of influenza virus and/or to the additional antigen(s).

Administration of the (immunogenic) compositions according to the disclosure can be performed using standard routes of administration. Non-limiting examples include parenteral administration, such as intravenous, intradermal, transdermal, intramuscular, subcutaneous, etc., or mucosal administration, e.g., intranasal, oral, and the like. In certain embodiments, the virosomal preparations and/or immunogenic compositions are administered more than one time, i.e., in a so-called homologous prime-boost regimen. In certain embodiments where the virosomal preparations and/or immunogenic compositions are administered more than once, the administration of the second dose can be performed after a time interval of, for example, one week or more after the administration of the first dose, two weeks or more after the administration of the first dose, three weeks or more after the administration of the first dose, one month or more after the administration of the first dose, six weeks or more after the administration of the first dose, two months or more after the administration of the first dose, three months or more after the administration of the first dose, four months or more after the administration of the first dose, etc., up to several years after the administration of the first dose of the virosomal preparations and/or immunogenic compositions. It is also possible to administer the virosomal preparations and/or immunogenic compositions more than twice, e.g., three times, four times, etc., so that the first priming administration is followed by more than one boosting administration. In other embodiments, the virosomal preparations and/or immunogenic compositions according to the disclosure are administered only once. The virosomal preparations and/or immunogenic compositions may also be administered, either as prime, or as boost, in a heterologous prime-boost regimen.

In certain embodiments, prevention and/or treatment may be targeted at patient groups that are susceptible to infection with the virus, in particular, to influenza virus infection. Such patient groups include, but are not limited to, e.g., the elderly (e.g., ≥50 years old, ≥60 years old, and preferably ≥65 years old), the young (e.g., ≤5 years old, ≤1 year old), hospitalized patients and patients who have been treated with an antiviral compound but have shown an inadequate antiviral response.

In other embodiments, the virosomal preparations and/or immunogenic compositions may be administered to a subject in combination with one or more other active agents, such as existing vaccines, monoclonal antibodies and/or antiviral agents, and/or antibacterial agents, and/or immunomodulatory agents.

This disclosure is further illustrated in the following Examples.

EXAMPLES

Example 1

Virosome Preparation According to the Disclosure

Solubilization of the Inactivated Virus Bulk and Phospholipids

The inactivated virus bulk (IVB, A. California, A. Victoria or B. Brisbane) was diluted with phosphate-buffered saline (PBS, pH 7.4), mixed with a magnetic stirrer and divided into ultracentrifugation (UC) bottles, followed by ultracentrifugation for 1 hour. The supernatant of all the UC bottles/tubes were discarded and 100 mM OEG solution (55% of required volume) serially added to resuspend the pellet in different bottles. The ultracentrifugation bottles/tubes were rinsed serially with additional 100 mM OEG solution (35% of required volume), and pooled with the first suspension and the resuspended pellet stirred overnight at 4° C. The resuspended pellet was divided in the ultracentrifugation bottles/tubes, and ultracentrifuged. The supernatant was gently withdrawn from the bottle/tube into a clean glass bottle without disturbing the pellet in the bottom of the tube. The phospholipids (PL) were weighed directly into a clean glass vial and the OEG solution (10% of required volume) added and mixed with magnetic stirrer overnight at 2° C. to 8° C. for solubilization. The PL suspension and supernatant containing viral envelope material were combined and mixed for 30-60 minutes at room temperature (15° C. to 25° C.) until the mixture was free of any visible particles.

Preparation of BIOBEADS®

BIOBEADS® were weighed into a glass flask, methanol added and stirred for 10 minutes followed by filtration to remove the methanol. This was repeated with demineralized water. Residual moisture content of 1 gram of BIOBEADS® was determined using a halogen moister analyzer. Thereafter, the BIOBEADS® were subdivided into two bottles (bottle A and bottle B), water was added and the bottles were autoclaved, and subsequently stored at 2° C. to 8° C. until used.

Virosome Formation by OEG Removal with BIOBEADS®

Water was removed from batch chromatography bottle A using a syringe and needle. The supernatant with PL was transferred into bottle A, placed in a turbula shaker and shaken at 23 rpm for 1 hour at room temperature to remove the OEG. Water was removed from batch chromatography Bottle B as well. The suspension from bottle A was transferred to bottle B and the bottle placed in the turbula shaker and shaken at 23 rpm for 1 hour at RT to complete removal of the OEG. The virosomes formed (raw monovalent virosome) were collected, the HA content determined and thereafter diluted with PBS pH 7.4 accordingly to yield HA concentration of 150 to 300 μg/mL. The raw monovalent virosome was filtrated using a 0.22 μm filter and stored at 2° C. to 8° C. until used.

Example 2

Virosome Preparation According to the Prior Art

Solubilization of the Inactivated Virus Bulk and Phospholipids

The inactivated virus bulk (IVB, A. California, A. Victoria or B. Brisbane) was diluted with phosphate-buffered saline (PBS, pH 7.4), mixed with a magnetic stirrer and aliquoted into ultracentrifugation (UC) bottles, followed by ultracentrifugation for 1 hour at 25000 rpm in a Beckman type 45Ti rotor or equivalent at room temperature. The supernatant of all the UC bottles were discarded and 100 mM OEG solution (90% of required volume) added to resuspend the pellet in different bottles. The ultracentrifugation bottles/tubes were rinsed with additional 100 mM OEG solution (10% of required volume), and pooled with the first suspension and the resuspended pellet stirred overnight at 4° C. to solubilize the viral envelope. The resuspended pellet was divided in the ultracentrifugation tubes, and ultracentrifuged. The supernatant was gently withdrawn from the tubes into a clean glass bottle without disturbing the pellet in the bottom of the tube. The phospholipids (PL) were weighed directly into the bottle and sonicated at 100% output and mixed with a syringe at 33° C. to 37° C., and repeated until complete solubilization of the PL. The dissolution rate of PL appeared to be batch size dependent. The larger the batch size, the longer the dissolution time needs. For production scale, the PL formed lumps and were not solubilized even after 80 minutes ultrasonification.

Preparation of BIOBEADS®

The BIOBEADS® were weighed into a glass flask, methanol added and stirred for 10 minutes followed by filtration to remove the methanol. This was repeated with demineralized water. Residual moisture content of 1 gram of BIOBEADS® was determined using a halogen moister analyzer. Thereafter, the BIOBEADS® were subdivided into two bottles (bottle A and bottle B); water was added and the bottles were autoclaved and subsequently stored at 2° C. to 8° C. until used.

Virosome Formation by OEG Removal with BIOBEADS®

Water was removed from batch chromatography bottle A using a syringe and needle. The supernatant with PL was transferred into bottle A, placed in a turbula shaker and shaken at 23 rpm for 1 hour at room temperature to remove the OEG.

Water was removed from batch chromatography Bottle B as well. The suspension from bottle A was transferred to bottle B and the bottle placed in the turbula shaker and shaken at 23 rpm for 1 hour at RT to complete removal of the OEG. The virosomes formed (raw monovalent virosome) was collected, the HA content determined and thereafter diluted with PBS pH 7.4 accordingly to yield HA concentration of 150 to 600 μg/mL. The raw monovalent virosome was filtrated using a 0.22 μm filter and stored at 2° C. to 8° C. until use.

What is claimed is:

1. A method for preparing virosomes, the method comprising
solubilizing viral envelopes in a first solubilizing agent by stirring at a temperature of between 2-8° C. overnight;
pre-solubilizing exogenous components in a second solubilizing agent by stirring at a temperature of between 2-8° C. overnight;
adding the pre-solubilized exogenous components to the solubilized viral envelopes by stirring at a temperature below 33° C. for 30-60 minutes; and
reconstituting virosomal membranes therefrom by removing the solubilizing agent;
wherein the step of adding the pre-solubilized exogenous components to the solubilized viral envelopes does not involve the use of sonication or centrifugation.

2. The method according to claim 1, wherein the first and second solubilizing agents are the same.

3. The method according to claim 2, wherein the viral envelopes are solubilized using from 20-99% of a total amount of the solubilizing agent and the exogenous components are pre-solubilized using from 1-80% of the total amount of the solubilizing agent.

4. The method according to claim 1, wherein the solubilizing agent is octaethylene glycol monododecyl ether (OEG).

5. The method according to claim 4, wherein the solubilizing agent is used in a concentration of about 10-1000 mM.

6. The method according to claim 5, wherein the exogenous components are exogenous lipids.

7. The method according to claim 6, wherein the lipids are egg-derived phospholipids.

8. The method according to claim 1, further comprising: purifying the reconstituted virosomes.

9. The method according to claim 1, wherein the enveloped virus is an influenza virus.

10. The method according to claim 1, wherein the viral envelopes have been inactivated before solubilization in the first solubilizing agent.

11. The method according to claim 5, wherein the solubilizing agent is used in a concentration of about 50-250 mM.

12. The method according to claim 7, wherein the lipids comprise egg phosphatidylcholine.

13. A method of preparing a virosome, the method comprising:
solubilizing a viral envelope in octaethylene glycol monododecyl ether (OEG) by stirring at a temperature of between 2-8° C. overnight;
pre-solubilizing exogenous lipids in OEG by stirring at a temperature of between 2-8° C. overnight;
adding the pre-solubilized exogenous lipids to the viral envelope solubilized in OEG by stirring at a temperature below 33° C. for 30-60 minutes; and
reconstituting a virosomal membrane therefrom by removing the OEG;
wherein the step of adding the pre-solubilized exogenous lipids to the viral envelope solubilized in OEG does not involve the use of sonication or centrifugation.

14. The method according to claim 13, wherein the viral envelopes have been inactivated before solubilization in the OEG.

15. The method according to claim 13, wherein the OEG is utilized at a concentration of about 50-250 mM.

16. The method according to claim 13, wherein the exogenous lipids comprise egg phosphatidylcholine.

* * * * *